United States Patent [19]

Van Driel

[11] Patent Number: 5,759,396
[45] Date of Patent: Jun. 2, 1998

[54] CARDIOTOMY FILTER/DEFOAMER STRUCTURE WITH THREE-STAGE FILTER/DEFOAMER

[75] Inventor: Michael R. Van Driel, Fountain Valley, Calif.

[73] Assignee: Medtronic, Inc., Minneapolis, Minn.

[21] Appl. No.: 728,874

[22] Filed: Oct. 10, 1996

[51] Int. Cl.⁶ .................................................. B01D 36/02
[52] U.S. Cl. .......................... 210/315; 96/179; 210/335; 210/436; 210/489; 604/4; 604/319
[58] Field of Search .................................. 210/188, 314, 210/315, 335, 337, 338, 436, 438, 455, 472, 483, 484, 488, 489, 490, 510.1, 645; 604/4, 317, 319, 410; 422/44–48; 96/176, 178, 179

[56] References Cited

U.S. PATENT DOCUMENTS

| | | | |
|---|---|---|---|
| 4,704,203 | 11/1987 | Reed | 210/489 |
| 4,743,371 | 5/1988 | Servas et al. | 96/179 |
| 5,127,900 | 7/1992 | Schickling et al. | 604/4 |
| 5,158,533 | 10/1992 | Strauss et al. | 604/4 |
| 5,411,705 | 5/1995 | Thor et al. | 210/436 |

OTHER PUBLICATIONS

Medtronic 1991 Product Data Sheet for "Maxima Hardshell Venous Reservoir".

*Primary Examiner*—Joseph W. Drodge
*Attorney, Agent, or Firm*—Harry G. Weissenberger

[57] ABSTRACT

A three-stage cardiotomy filter/defoamer dispenses with the conventional tricot sock covering by forming the secondary defoamer as a small-pore foam impregnated with a much heavier concentration of defoaming agent than the primary large-pore defoamer.

5 Claims, 2 Drawing Sheets

CARDIOTOMY FILTER/DEFOAMER STRUCTURE WITH THREE-STAGE FILTER/DEFOAMER

FIELD OF THE INVENTION

This invention relates to filter/defoamers for hardshell venous blood reservoirs, and more particularly to a filter/defoamer construction using only three stages of cardiotomy blood filtration and defoaming.

BACKGROUND OF THE INVENTION

Hardshell venous reservoirs are used in cardiac surgery to receive and store the patient's venous blood, and to dispense it as needed to the oxygenating heart-lung machine. Venous blood has a high flow rate but is clean and needs only relatively little defoaming, mostly for removal of microair, before being stored in the reservoir.

Another source of blood for the heart-lung machine is the cardiotomy blood recovered by suction from the surgical field. This blood has a low flow rate but is heavily aerated (i.e. foamy) and contains a substantial amount of cell or surgical debris. Consequently, it requires considerable defoaming and filtering before being reused.

Originally, cardiotomy blood and venous blood were processed and stored in separate reservoirs because of their very different flow rates and processing needs. During that time, a cardiotomy filter/defoamer construction, such as that shown in U.S. Pat. No. 4,743,371, was developed using a four-stage filtering/defoaming process. In that process, cardiotomy blood first flowed through a primary defoamer layer of defoaming chemical impregnated porous polyurethane with a porosity on the order of 8 pores per centimeter (ppc), then through a felt filter, thirdly through a secondary 8 ppc urethane foam layer impregnated with a defoaming chemical, and finally through a polyknit sock surrounding the filter/defoamer assembly. The function of the polyknit sock was to slow the blood flow through the filtering and defoaming layers so as to lengthen the time that the blood would be in contact with the defoaming chemical. The sock also acted as a coarse secondary filter capable of trapping any relatively large particles which had somehow passed through the felt filter.

In recent years, the trend has been to combine the cardiotomy reservoir with the venous reservoir in a single hardshell venous reservoir in which venous blood and cardiotomy blood are introduced into separate sections of a common defoaming structure located in the reservoir. In this type of structure, the use of a polyknit or tricot sock is undesirable because it slows not only the cardiotomy blood flow, but also the venous flow. This is undesirable because the venous flow is a high-volume flow and needs little defoaming. In addition, the polyknit material brings another artificial material into contact with the blood, which is medically undesirable.

SUMMARY OF THE INVENTION

The present invention allows omission of the prior art's polyknit sock without forgoing its flow retarding and secondary filtering function by forming the secondary defoamer from a thinner layer of porous polyurethane foam with substantially smaller pores, e.g. on the order of 18–40 ppc, and using a much higher concentration of defoaming agent in that layer. This construction essentially maintains the amount of contact between the blood and the defoaming chemical in the cardiotomy filter/defoamer without inordinately impeding venous blood flow. At the same time, the construction of this invention is effective in quickly removing microair in the venous flow. Also, the absence of the tricot sock eliminates one of the types of artificial materials that come in contact with the blood in the reservoir.

DESCRIPTION OF THE PREFERRED EMBODIMENT

Figure 1:
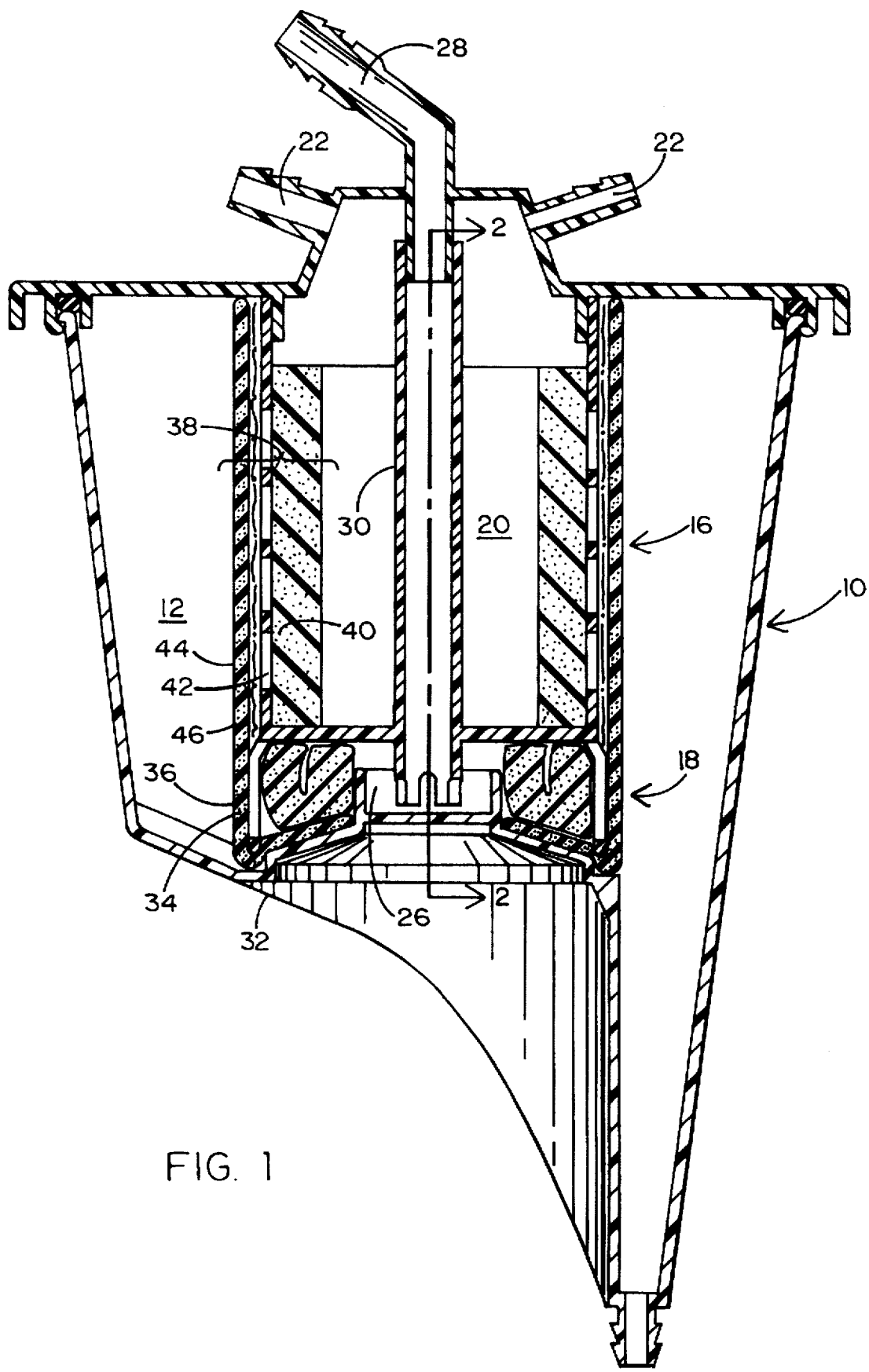
FIG. 1 is an axial section of a hardshell venous reservoir using the invention.
Figure 2:
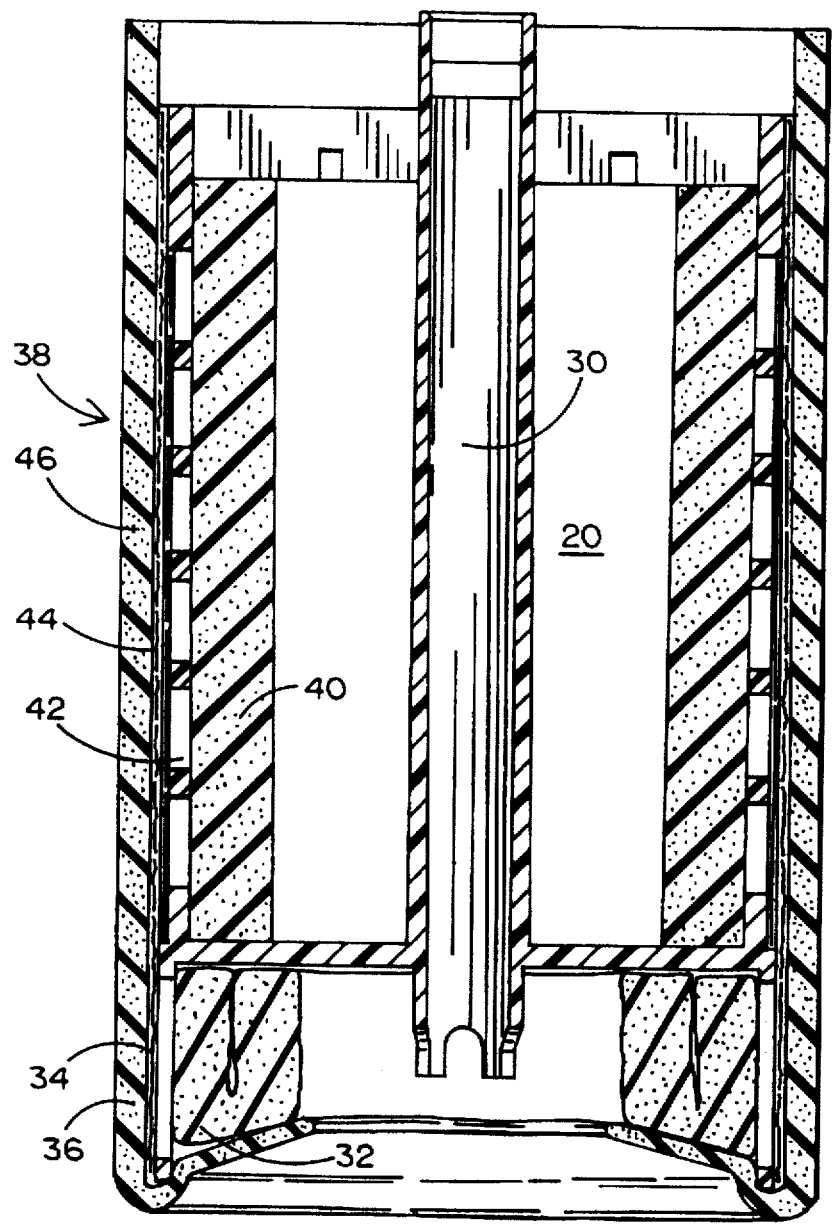
FIG. 2 is an enlarged section along line A—A of FIG. 1.

As shown in the drawings, the hardshell combination venous reservoir and cardiotomy filter/defoamer 10 of this invention has a polycarbonate reservoir body 12 and a circumferentially apertured high-impact polystyrene frame 14 which supports the cardiotomy filter/defoamer section 16 and the venous defoamer section 18. Cardiotomy blood enters the cardiotomy chamber 20 through the cardiotomy connectors 22 in the cover 24, while venous blood enters the venous chamber 26 from the venous connector 28 via the flow tube 30. From the venous chamber 26, venous blood is discharged into the reservoir body 12 through a large-pore (e.g. 8 ppc) porous polyurethane defoamer ring 32 coated with a suitable defoaming chemical such as, e.g., Dow silicone antifoam A; then through frame apertures 34; and finally through a small-pore (e.g. 18 ppc) porous polyurethane defoamer mantle 36. In accordance with the invention, the mantle or layer 36 is coated with the above-mentioned defoaming chemical at the rate of about 2.25–4.5 mg/cm$^3$ as opposed to the conventional concentration of about 0.5 mg/cm$^3$ used in the large pore defoamer ring 32.

Cardiotomy blood enters the annular filter/defoamer structure 38 from the cardiotomy chamber 20 through a cylindrical porous polyurethane foam layer 40 which is coated with a conventional defoaming agent at a concentration of about 0.5 mg/cm$^3$, and whose porosity is preferably about 8–10 ppc. It next passes outwardly through windows 42 in the rigid polystyrene frame 14 to a polyester felt filter 44. The filtered blood then proceeds through a second porous polyurethane foam layer 46 impregnated with a high level (e.g. 2.25–4.5 mg/cm$^3$) of defoaming agent. The porosity of the layer 46 is preferably about 18–40 ppc. The layer 46 is preferably part of the mantle 36 which uniformly surrounds the entire frame 14.

It is understood that the exemplary hardshell venous reservoir with three-stage filter defoamer described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A cardiotomy filter/defoamer structure comprising, as arranged in a direction of cardiotomy blood flow:

a) a primary defoamer consisting of a relatively large-pored porous foam impregnated with an anti-foaming agent at a first concentration;

b) an apertured support structure;

c) a biocompatible felt depth filter mounted on said support structure; and d) a secondary defoamer consisting of a substantially smaller-pored porous foam impregnated with an antifoaming agent at a second, substantially higher, concentration.

2. The structure of claim 1, in which said antifoaming agent is silicone, said first concentration is substantially 0.5 mg/cm$^3$, and said second concentration is substantially 2.25–4.5 mg/cm$^3$.

3. The structure of claim 1, in which said large-pored foam has a pore size of substantially 8–10 pores per centimeter, and said small-pored foam has a pore size of substantially 18–40 pores per centimeter.

4. A combined cardiotomy filter/defoamer and venous microair defoamer structure for a hardshell venous reservoir, comprising:
   a) a cardiotomy filter/defoamer structure including, as arranged in a direction of cardiotomy blood flow:
      i) a primary defoamer consisting of a relatively large-pored porous foam impregnated with an antifoaming agent at a first concentration;
      ii) an apertured support structure;
      iii) a biocompatible filter mounted on said support structure; and
      iv) a secondary defoamer consisting of a substantially smaller-pored porous foam impregnated with an antifoaming agent at a second, substantially higher, concentration; and
   b) a venous microair defoamer structure including, as arranged in a direction of venous blood flow:
      i) a primary defoamer consisting of a relatively large-pored porous foam impregnated with an antifoaming agent at a first concentration; and
      ii) a secondary defoamer consisting of a substantially smaller-pored porous foam impregnated with an antifoaming agent at a second, substantially higher, concentration.

5. The structure of claim 4, in which a single secondary defoamer envelops both said cardiotomy filter/defoamer structure and said venous microair defoamer structure.

* * * * *